US007918841B2

(12) United States Patent
Sinha et al.

(10) Patent No.: US 7,918,841 B2
(45) Date of Patent: Apr. 5, 2011

(54) DEVICES AND METHODS FOR NASOENTERIC INTUBATION

(75) Inventors: Ashish C. Sinha, Philadelphia, PA (US); Owen J Halloran, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 61 days.

(21) Appl. No.: 12/418,464

(22) Filed: Apr. 3, 2009

(65) Prior Publication Data

US 2009/0306626 A1 Dec. 10, 2009

Related U.S. Application Data

(60) Provisional application No. 61/064,934, filed on Apr. 3, 2008.

(51) Int. Cl.
*A61M 39/00* (2006.01)

(52) U.S. Cl. ........................ 604/516; 604/275; 604/265

(58) Field of Classification Search ................. 604/516, 604/275, 265; 128/200.26
See application file for complete search history.

*Primary Examiner* — Kevin C Sirmons
*Assistant Examiner* — Michael J Anderson
(74) *Attorney, Agent, or Firm* — Pearl Cohen Zedek Latzer, LLP; Mark S. Cohen

(57) ABSTRACT

This invention relates to the placement of nasogastric tubes. Specifically, the present invention relates to devices, methods, and kits for assisting intubation and insertion.

22 Claims, 3 Drawing Sheets

DEVICES AND METHODS FOR NASOENTERIC INTUBATION

CROSS REFERENCE TO RELATED APPLICATIONS

This application claims priority to U.S. Provisional Patent Application 61/064,934, filed Apr. 3, 2008, which is incorporated herein in its entirety.

FIELD OF THE INVENTION

This invention is directed to the placement of nasogastric tubes. Specifically, the present invention relates to a device that assists intubation and insertion.

BACKGROUND OF THE INVENTION

The medical industry uses nasogastric tube devices for many reasons including diagnosis of gastrointestinal disease, decompression of the gastrointestinal tract, delivery of medication and nutrition, and research, among others. It has been suggested that at least one million enteral tubes are placed annually. It is thought that this number is probably underestimated.

Placement of nasogastric tubes continues to expose patients to significant risks. The incidence of complications from nasogastric tube placement has been estimated to be between 1.3 and 89.5% depending on the definition of complication. There are a vast number of case reports in the medical literature of devastating complications of nasogastric tube insertion including placement into the submucosa of the nasopharynx, placement into the brain, perforation into the neck and spine, and placement into the trachea, bronchi, and lungs. These complications are typically the result of perforation of the nasal passage, nasopharynx, or passage into the trachea. In addition, nasal-bleeding and local trauma to the nasal passage and nasopharynx are common.

No reliable and safe technique exists for placing nasogastric devices. There are descriptions of techniques which require the use of endoscopy, direct laryngoscopy, or complicated manipulation of pre-existing equipment designed for other purposes. However, most nasogastric tubes are placed blindly. This presents a particular challenge with intubated or comatose patients who are unable to swallow, indicate pain, or faulty passage of a nasogastric tube.

SUMMARY OF THE INVENTION

In one embodiment, the invention provides a device for introducing nasoenteric intubation in a subject. The device may include a tube having a first end, a second end, and three sections separated by two inflection regions between said first and second ends, said tube further having a guideline extending dorsally along said tube from said first end along a first section, a first inflection region and a first portion of a second section of said tube, passing circumferentially about said tube within said second section from a dorsal position to a ventral position, and extending ventrally along said tube along a second portion of said second section, a second inflection region and a third section of said tube to said second end.

In another embodiment, the invention provides a method of nasoenterically intubating a subject in need thereof. The method may include the steps of: inserting into the nasal passage of a subject, second end first, a device for introducing nasoenteric intubation in a subject, the device including: a tube having a first end, a second end, three sections separated by two inflection regions between said first and second ends, and a guideline extending dorsally along said tube from said first end along a first section, a first inflection region and a first portion of a second section of said tube, passing circumferentially about said tube within said second section from a dorsal position to a ventral position, and extending ventrally along said tube along a second portion of said second section, a second inflection region and a third section of said tube to said second end, while maintaining the guideline on a side of the tube remote from said subject while inserting the device; and inserting a nasoenteric intubation device through the tube.

In one embodiment, the invention provides a kit. The kit may include a device for introducing nasoenteric intubation in a subject, the device including: a tube having a first end, a second end, three sections separated by two inflection regions between said first and second ends, and a guideline extending dorsally along said tube from said first end along a first section, a first inflection region and a first portion of a second section of said tube, passing circumferentially about said tube within said second section from a dorsal position to a ventral position, and extending ventrally along said tube along a second portion of said second section, a second inflection region and a third section of said tube to said second end; and a nasoenteric intubation device.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE INVENTION

This invention relates in one embodiment to the placement of nasogastric tubes. In another embodiment, the invention provides devices methods and kits directed to intubation insertion.

The danger with blind passage of nasogastric tube stems from three properties of currently available nasogastric tube devices: their small external diameter, rigidity, and length. The small external diameter and rigidity of a nasogastric tube give it the ability to perforate soft tissues. Its small diameter, length, and rigidity make it difficult to manipulate distally and gives it the ability to pass into the trachea. Its length makes it difficult to verify the position of its distal end as the operator will not know if has made it into the stomach or elsewhere until it has been inserted 40 cm.

Embodiments of the invention may circumvent these problems, allowing for the safe and easy guidance of nasogastric tubes into the esophagus. The large external diameter, softness, and flexibility of one embodiment may make it less likely to cause perforation or trauma to soft tissues of the nasal passage and nasopharynx. The sufficient rigidity, shape, and method of placement of one embodiment may allow for easy and reliable placement into the esophagus and away from the trachea.

Figure 1:
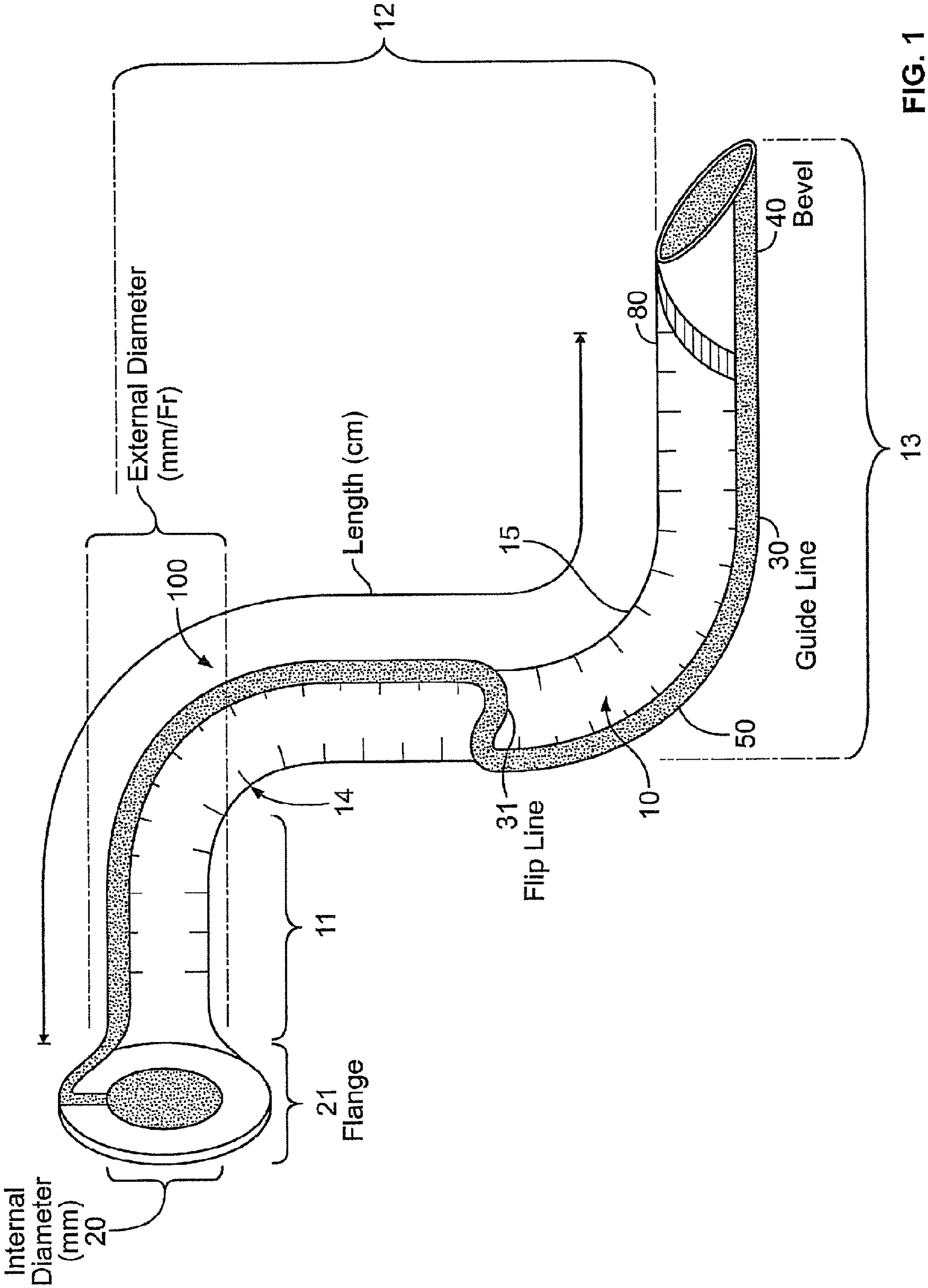
FIG. 1 shows an gastroenteric intubation tube according to one embodiment of the invention.

FIG. 1 depicts a nasoesophageal device 100 according to one embodiment. Nasoesophageal device 100 may be of any suitable shape, for example, but not limited to, S-shape, C-shape, and curved shape. In a particular embodiment, nasoesophageal device 100 may be able to maintain its shape before insertion, during insertion, and/or after insertion. The nasoesophageal device 100 may include a tube 10 having an interior surface extending between a first end 20 and an opposing second end 40, said tube having a circular or oval shaped wall in cross-section, said tube 10 having an open central passageway from said first end 20 to said second end 40, said open passageway being of sufficient diameter to allow the passage of any practical nasogastric device there through, said tube 10 having sufficient rigidity so that lumens and ducts formed in its walls will not readily collapse, said first end 20 arranged to be positioned externally of the patient at the patient's nares and said second end 40 arranged to be inserted into a nasal passage of a patient and positioned into the esophagus, a flange 21 at the first end 20 of said tube 10 of sufficient diameter to prevent further insertion of said device at the nares, said first end 20 and second end 40 of the tube 10 being adapted to be received within a nostril of a nasal passageway in opposing orientation such that the tube 10 resembles a sigmoid shape in any of three dimensions (or cork screw like in certain embodiments). Tube 10 may be of any length and combination of angles with markings running longitudinally along the outside of said tube 10 in one embodiment, such as to indicate the orientation of said tube 10 and depth of insertion.

Further with regard to FIG. 1, nasoesophageal device 100 may include a tube 10 having a first end 20, a second end 40, and three sections 11, 12, and 13 separated by two inflection regions (14, 15) between said first 20 and second ends 40, said tube 10 further having a guideline 30 extending dorsally along said tube 10 from said first end 20 along a first section 11, a first inflection region 14 and a first portion of a second section 12 of said tube 10, passing circumferentially about said tube 10 within said second section 12 from a dorsal position to a ventral position, and extending ventrally along said tube 10 along a second portion of said second section 12, a second inflection region and a third section 13 of said tube 10 to said second end. The cross section of tube 10 may be of any suitable shape, for example, but not limited to, circle, oval, and ellipse. In one embodiment, a radio-opaque stripe 50 and/or distance marks in a longitudinal or radial arrangement are disposed along said tube 10. In some embodiments, tube 10 may include a scale-marking on its surface that helps determine the depth of insertion of a device inserted into said tube 10.

When used herein, ventral and dorsal are relative terms. Ventral and dorsal are chosen because of the expected orientation of device 10 when inserted into a subject as intended. However, other terms (e.g., front/back, top/bottom) may be used.

The tube 10 may be for example made of a resilient biocompatible material, such as surgical grade stainless steel, polycarbonate, poly(Methymethacrilate), polyamide-ether block copolymer, polyether-ester block copolymer, polyester-ester block copolymer, polyester-urethane block copolymer, polyether-urethane block copolymer, polycarbonate-urethane block copolymer, polyolefin, or polyolefin block copolymer. In one embodiment, the resilient biocompatible material is substantially transparent. In one embodiment, the tube 10 is puncture and tear resistant. The tube 10 may be of plastic, rubber, silicone, foamed polymer, other hypo-allergenic or flexible material, or a combination thereof in either a hard, semi hard, or semi soft configuration. Other materials may be used.

In one embodiment, the guideline 30 protrudes from tube 10 or provides a visual indication, or both, along an outer surface of said tube 10, and/or acts as a reinforcing member disposed along the length of said tube 10. In some embodiments, the first end 20 of said tube is flared, forming a flange 21 and in one embodiment, the second end 40, which is weighted in certain embodiments, is beveled, includes a hollow pencil point shaped tip, or is rounded. In some embodiments, an inflatable cuff, known to one of skilled in the art, may be associated with the second end 40 of said tube 10 positioned and adapted to engage the patient's nasopharynx or first esophagus.

In one embodiment, the tube 10 includes a therapeutically effective coating 80, such as an analgesic, a lubricant, a sedative, an anti-inflamatory or their combination. Other therapeutically effective coatings may be used.

In one embodiment, the degree of curvature of said tube 10 is adjustable, such that the spatial relationship among sections 11, 12 and 13 is not a constant, but can change without affecting the resiliency of the tube 10. In another embodiment, the curvature is adjustable to conform to the nasal passages of the subject, prior to insertion of the devices provided herein, using the methods described herein.

In one embodiment, said tube 10 is include a plurality of spaced apart openings extending through the tube 10 so as to communicate with the air or food passage. In another embodiment, the tube 10 used in the devices provided herein, includes a shear line, known to one of skilled in art, formed by, for example, a longitudinal, linearly weakened portion. In one embodiment, the nasoesophageal device 100 contains a lumen formed within the wall of said tube 10 and extending the length thereof which allows connectivity to an airway gas analyzer, or in another embodiment, the tube 10 includes a member disposed along the length of the tube that changes color in the response to pH.

In some embodiments, nasoesophageal device 100 may be coupled to a nasal attachment device that enables to hold nasoesophageal device 100 on a subject's nasal region. In a particular embodiment, the nasal attachment device includes a ring, for example, a D-shaped ring. At least one portion of the ring has an ability or otherwise a mechanism for placing the ring adjacent to subject's lips. The nasal attachment device may be made of any suitable material, for example, a rubber material. The nasal attachment device may include circumferential perforations. In some embodiments, the nasal attachment device helps avoid pressure on nose, and thereby avoid necrosis and/or other complications of long-term placements. In some embodiments, nasoesophageal device 100 may be coupled to a device, for example, an adopter that measures $CO_2$. In one example, nasoesophageal device 100 may be coupled to a calorimetric adopter. Other suitable adopters may also be used.

Figure 2:
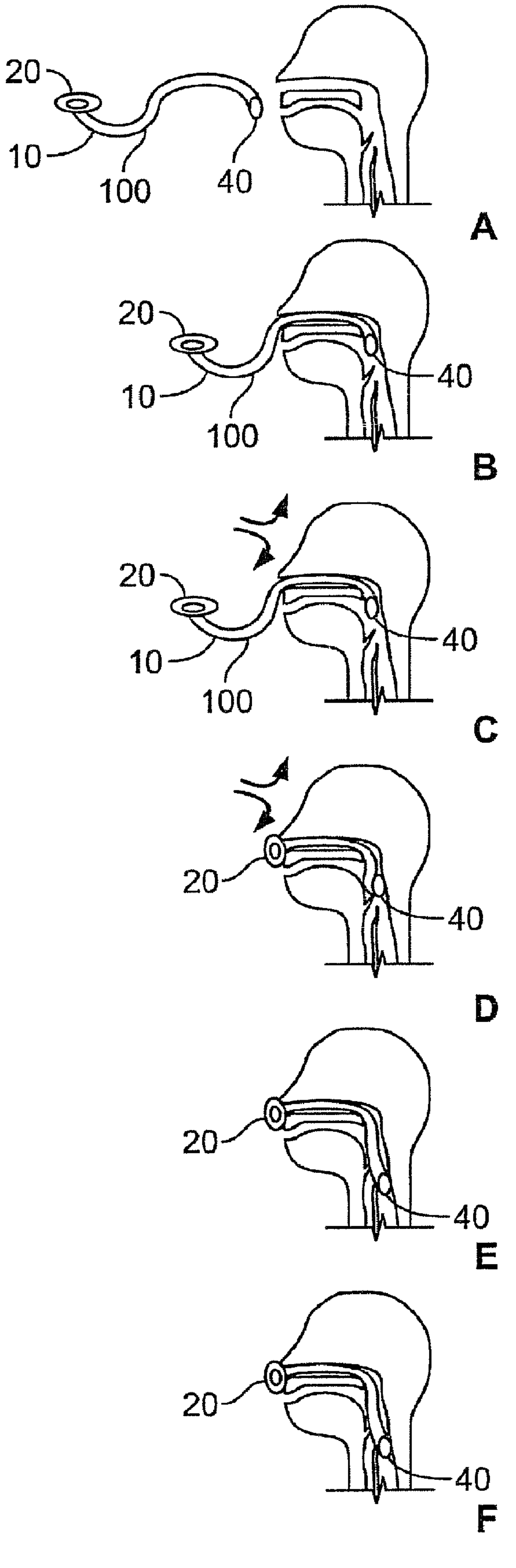
FIG. 2 shows a nasoesophageal device being introduced to relevant anatomy according to one embodiment of the invention.

Turning now to FIG. 2, FIG. 2A shows the nasoesophageal device 100 and relevant anatomy. FIG. 2B shows that the nasoesophageal device 100 is introduced into the nares and gently advanced along its natural curvature following the shape of the nasopharynx. FIG. 2C shows that the nasoesophageal device 100 is gently advanced as its shape follows the curve of the nasal passageway and nasopharynx. FIG. 2D shows that as the nasoesophageal device 100 is gently advanced and/or twisted such that the second end begins to hug the posterior pharynx. FIG. 2E shows that the nasoesophageal device 100 selectively reaches the esophagus and creates a passageway for any practical nasogastric device to be directed towards and thereby reach the stomach. FIG. 2F shows that any reasonable nasogastric device is reliably and safely guided into the stomach. In some embodiments, nasoesophageal device 100 described herein may be inserted through a patient's nasal passage such that the second end 40 is oriented such that its natural curvature will follow the natural shape of the nasopharynx. The nasoesophageal device 100 is continually advanced and/or spirally advanced with the aid of longitudinal markings running along the outside of said device 100 in such a fashion that its natural shape conforms to the nasopharynx in such a way that the second end 40 begins to hug the posterior pharyngeal wall as it advances into the esophagus.

In one embodiment, the devices and nasoenteric intubation device inserted into the tube 10 of the devices described herein may be components of a kit. In some embodiments, a kit may include: a nasoesophageal device 100 for introducing nasoenteric intubation in a subject, the nasoesophageal device 100 having: an tube 10 having a first end 20, a second end 40, and three sections 11, 12, and 13 separated by two inflection regions (14, 15) between said first 20 and second ends 40, said tube 10 further having a guideline 30 extending dorsally along said tube 10 from said first end 20 along a first section 11, a first inflection region 14 and a first portion of a second section 12 of said tube 10, passing circumferentially about said tube 10 within said second section 12 from a dorsal position to a ventral position, and extending ventrally along said tube 10 along a second portion of said second section 12, a second inflection region and a third section 13 of said tube 10 to said second end 40; and a nasoenteric intubation device.

The devices described hereinabove are used in the methods described herein; however the methods described may use other devices. A method according to one embodiment includes nasoenterically intubating a subject in need thereof. The method may include the steps of: inserting into the nasal passage of a subject, the second end first 40 of a nasoesophageal device 100 for introducing nasoenteric intubation in a subject, the nasoesophageal device 100 including: a tube 10 having a first end 20, a second end 40, and three sections 11, 12, and 13 separated by two inflection regions (14, 15) between said first 20 and second ends 40, said tube 10 further having a guideline 30 extending dorsally along said tube 10 from said first end 20 along a first section 11, a first inflection region 14 and a first portion of a second section 12 of said tube 10, passing circumferentially about said tube 10 within said second section 12 from a dorsal position to a ventral position, and extending ventrally along said tube 10 along a second portion of said second section 12, a second inflection region and a third section 13 of said tube 10 to said second end 40, while maintaining the guideline 30 on a side of the tube 10 remote from said subject while inserting the device; and inserting a nasoenteric intubation device through the tube 10.

In another embodiment, the step of inserting the device is performed by: inserting into said subject's nose said second end 40, said third section 13, said second inflection region and said second portion of said second section 12 of said tube 10, such that the guideline 30 external to said subject is positioned on a side of the tube 10 remote from said subject during said insertion, when said second section 12 of said tube 10 where said guideline 30 passes circumferentially about said tube from a dorsal position to a ventral position is adjacent to said nose of said subject, rotating said device, if needed, about up to 180°, 31 such that the guideline external to said subject is positioned on a side of the tube 10 remote from said subject, and inserting into said subject's nose said first portion of said second section 12, said first inflection region and said first section 11 of said tube 10, such that the guideline 30 external to said subject is positioned on a side of the tube 10 remote from said subject.

Figure 3:
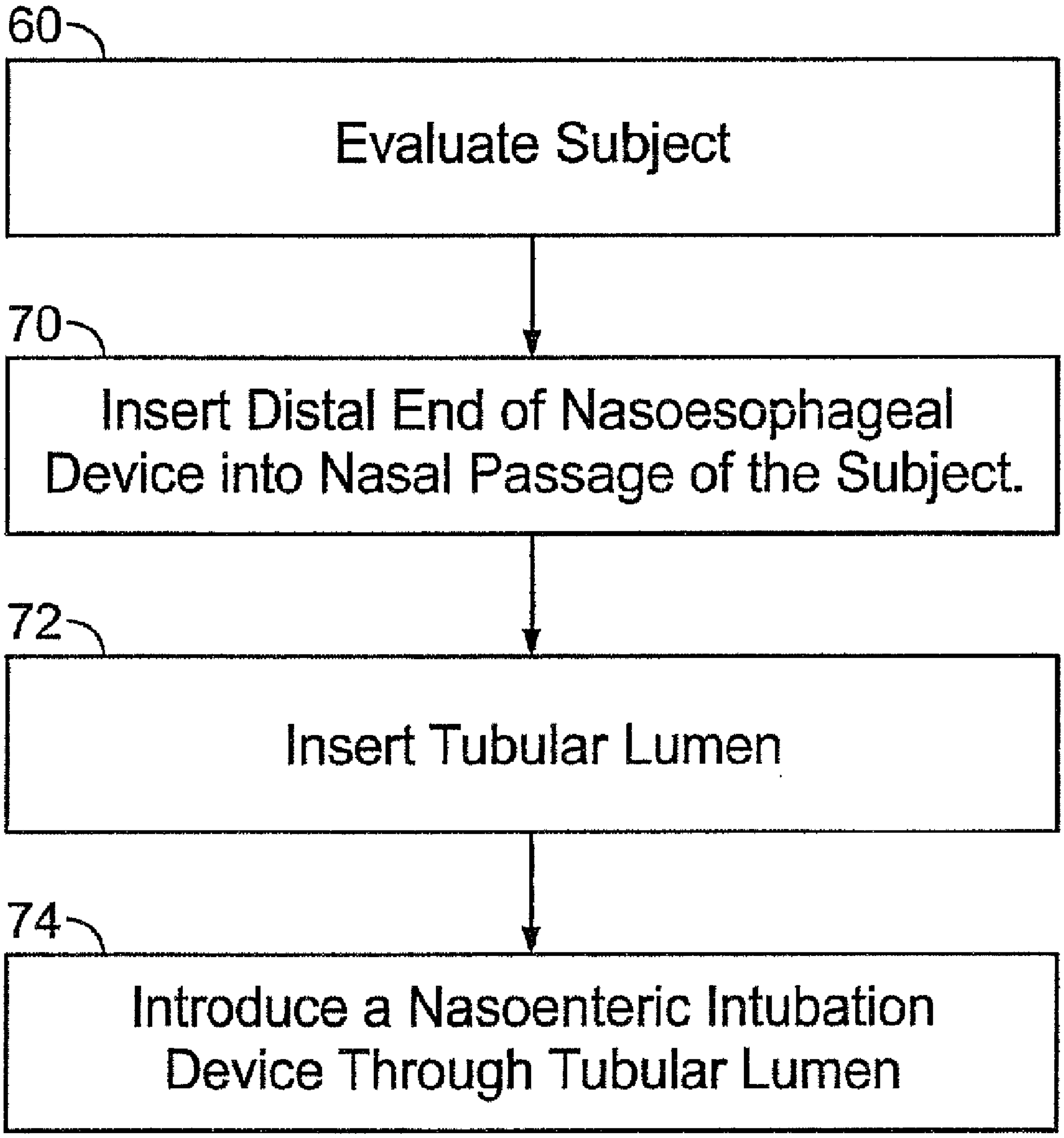
FIG. 3 illustrates a method of nasoenterically intubating a patient according to one embodiment of the invention.

As shown in FIG. 3, item 70, second end 40 of nasoesophageal device 100 is inserted in to a nasal passage of a subject. As shown in item 72, tube 10 is inserted in to the nasal passage. As shown in item 74, a nasoenteric intubation device, known to one of skilled in the art, is introduced through tube 10.

In one embodiment, the nasoenteric intubation device inserted into the tube 10 of the devices described herein, is a feeding tube, or a diagnostic angioscopy device, or a therapeutic agent delivery tube in certain other embodiments.

The term "about" as used herein means in quantitative terms plus or minus 5, or in another embodiment plus or minus 10%, or in another embodiment plus or minus 15%, or in another embodiment plus or minus 20%.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A device for introducing nasoenteric intubation in a subject, the device comprising: a tube having a first end, a second end, and three sections separated by two inflection regions between said first and second ends, said tube comprising a guideline extending dorsally along said tube from said first end along a first section, a first inflection region and a first portion of a second section of said tube, passing circumferentially about said tube within said second section from a dorsal position to a ventral position, and extending ventrally along said tube along a second portion of said second section, a second inflection region and a third section of said tube to said second end.

2. The device of claim 1, wherein the tube is graduated.

3. The device of claim 1, wherein said tube is made of a resilient biocompatible material.

4. The device of claim 3, wherein said resilient biocompatible material is substantially transparent.

5. The device of claim 3, whereby said resilient biocompatible material is surgical grade stainless steel, polycarbonate, poly(Methymethacrilate), polyamide-ether block copolymer, polyether-ester block copolymer, polyester-ester block copolymer, polyester-urethane block copolymer, polyether-urethane block copolymer, polycarbonate-urethane block copolymer, polyolefin, or polyolefin block copolymer.

6. The device of claim 1, wherein said guideline protrudes or provides a visual indication, or both, along an outer surface of said tube.

7. The device of claim 1, wherein said first end of said tube is flared.

8. The device of claim 1, wherein said second end of said tube is beveled.

9. The device of claim 1, wherein said tube comprises a therapeutically effective coating.

10. The device of claim 7, wherein the therapeutically effective coating is an analgesic, a lubricant, a sedative, an anti-inflamatory or their combination.

11. The device of claim 1, wherein the degree of curvature of said tube is adjustable.

12. The device of claim 9, wherein the curvature may be adjustable to conform to the nasal passages of the subject.

13. A method of nasoenterically intubating a subject in need thereof, comprising the steps of:

inserting into the nasal passage of a subject, second end first, a device for introducing nasoenteric intubation in a subject, the device comprising: a tube having a first end, a second end, three sections separated by two inflection regions between said first and second ends, and a guideline extending dorsally along said tube from said first end along a first section, a first inflection region and a first portion of a second section of said tube, passing circumferentially about said tube within said second section from a dorsal position to a ventral position, and extending ventrally along said tube along a second portion of said second section, a second inflection region and a third section of said tube to said second end, while maintaining the guideline on a side of the tube remote from said subject while inserting the device; and inserting a nasoenteric intubation device through the tube.

14. The method of claim 13, wherein the nasoenteric intubation device is adapted to be coupled to the flange at the first end of the tube.

15. The method of claim 13, wherein the degree of curvature of said tube is adjustable.

16. The method of claim 15, wherein the step of inserting the device is preceded by determining the degree of curvature of the subject's nasal passages.

17. The method of claim 16, wherein the step of determining is followed by adjusting the degree of curvature of said tube to conform to the nasal passages of the subject.

18. The method of claim 13, wherein the nasoenteric intubation device is a feeding tube, a diagnostic angioscopy device, or a therapeutic agent delivery tube.

19. The method of claim 13, wherein the step of inserting the device is performed by:

inserting into said subject's nose said second end, said third section, said second inflection region and said second portion of said second section of said tube, such that the guideline external to said subject is positioned on a side of the tube remote from said subject during said insertion, when said second section of said tube where said guideline passes circumferentially about said tube from a dorsal position to a ventral position is adjacent to said nose of said subject, rotating said device 180°, such that the guideline external to said subject is positioned on a side of the tube remote from said subject, and inserting into said subject's nose said first portion of said second section, said first inflection region and said first section of said tube, such that the guideline external to said subject is positioned on a side of the tube remote from said subject.

20. A kit comprising:

a device for introducing nasoenteric intubation in a subject, comprising: a tube having a first end, a second end, three sections separated by two inflection regions between said first and second ends, and a guideline extending dorsally along said tube from said first end along a first section, a first inflection region and a first portion of a second section of said tube, passing circumferentially about said tube within said second section from a dorsal position to a ventral position, and extending ventrally along said tube along a second portion of said second section, a second inflection region and a third section of said tube to said second end; and a nasoenteric intubation device.

21. The kit of claim 20, wherein the nasoenteric intubation device is a feeding tube, a diagnostic angioscopy device, or a therapeutic agent delivery tube.

22. The kit of claim 20, further comprising therapeutic agents, feeding material, or a combination thereof.

* * * * *